(12) United States Patent
Maltz

(10) Patent No.: US 10,722,731 B2
(45) Date of Patent: Jul. 28, 2020

(54) SYSTEM AND METHOD FOR PRETREATEMENT IMAGING IN ADAPTIVE RADIATION THERAPY

(71) Applicant: UIH-RT US LLC, Concord, CA (US)

(72) Inventor: Jonathan S. Maltz, Concord, CA (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 288 days.

(21) Appl. No.: 15/721,798

(22) Filed: Sep. 30, 2017

(65) Prior Publication Data

US 2019/0099619 A1   Apr. 4, 2019

(51) Int. Cl.
*A61N 5/10* (2006.01)

(52) U.S. Cl.
CPC ......... *A61N 5/1038* (2013.01); *A61N 5/1031* (2013.01); *A61N 5/1039* (2013.01); *A61N 5/1064* (2013.01); *A61N 5/1071* (2013.01)

(58) Field of Classification Search
CPC .. A61N 5/1038; A61N 5/1064; A61N 5/1071; A61N 5/1031
See application file for complete search history.

(56) References Cited

U.S. PATENT DOCUMENTS

| 6,142,925 A | 11/2000 | Siochi et al. |
| 2007/0041499 A1* | 2/2007 | Lu .......................... A61N 5/103 378/65 |
| 2015/0238779 A1* | 8/2015 | Marash ............... A61N 5/1049 600/1 |
| 2016/0114191 A1 | 4/2016 | Sankey |
| 2016/0125602 A1 | 5/2016 | Winfield et al. |
| 2018/0369611 A1* | 12/2018 | Owens ................. A61N 5/1031 |
| 2019/0076671 A1* | 3/2019 | Willcut ................ A61N 5/1031 |

OTHER PUBLICATIONS

First Office Action in Chinese Application No. 201810684445.4 dated Dec. 30, 2019, 20 pages.

* cited by examiner

*Primary Examiner* — Yara B Green
(74) *Attorney, Agent, or Firm* — Metis IP LLC

(57) ABSTRACT

A system and method for adapting treatment plan are provided. The method may include: obtaining a planning image of a region of interest relating to a first treatment fraction of a first treatment plan; obtaining a first image of the region of interest relating to a first scan of the region of interest with a first dose level; comparing the planning image with the first image to generate a first comparison result; determining whether the first comparison result satisfies a first replanning condition; causing, in response to a determination that the first comparison result satisfies the first replanning condition, one or more scanners to perform a second scan with a second dose level to provide a second image; and generating a second treatment plan according to the second image, wherein the second dose level is higher than the first dose level.

23 Claims, 6 Drawing Sheets

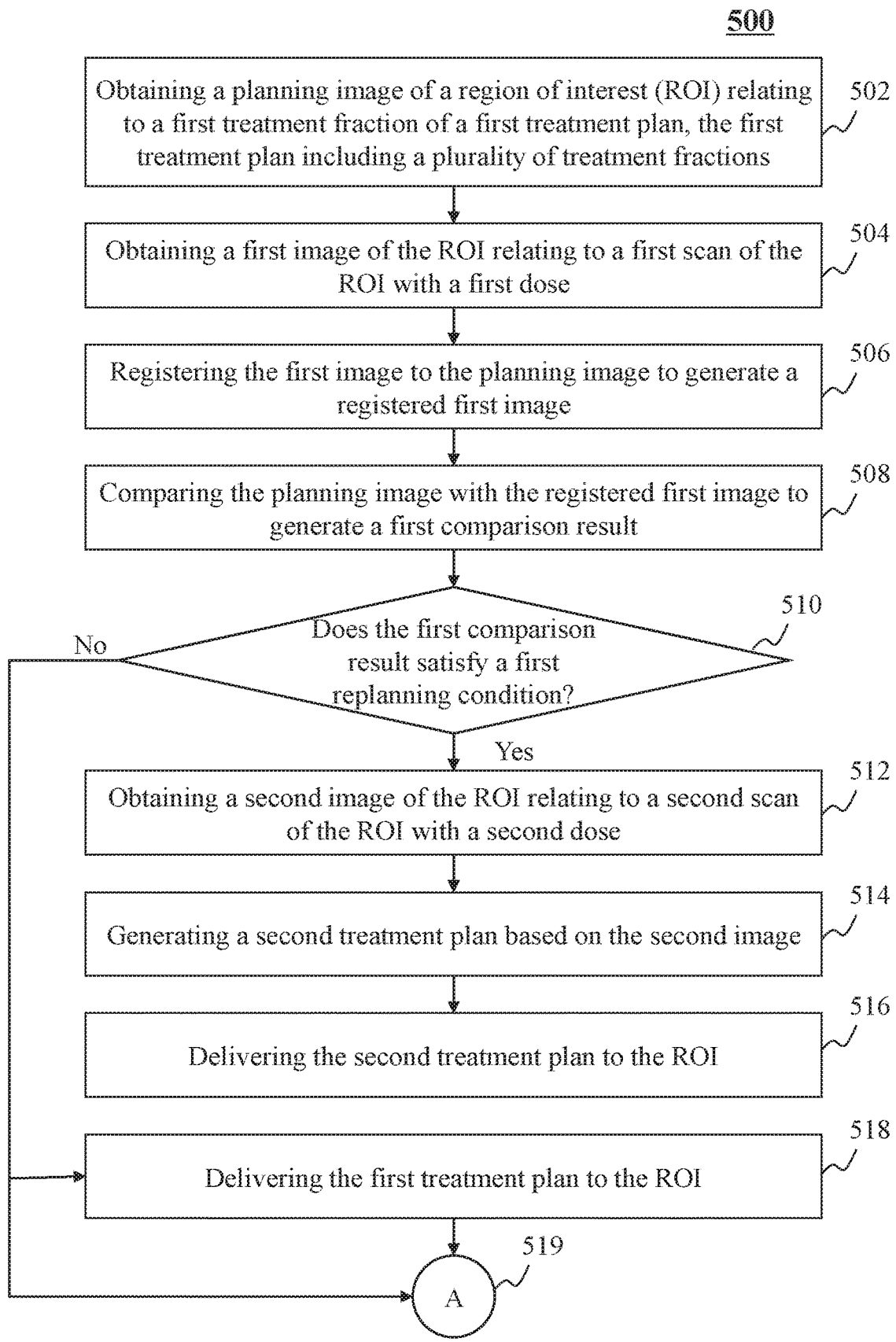
FIG. 5-A

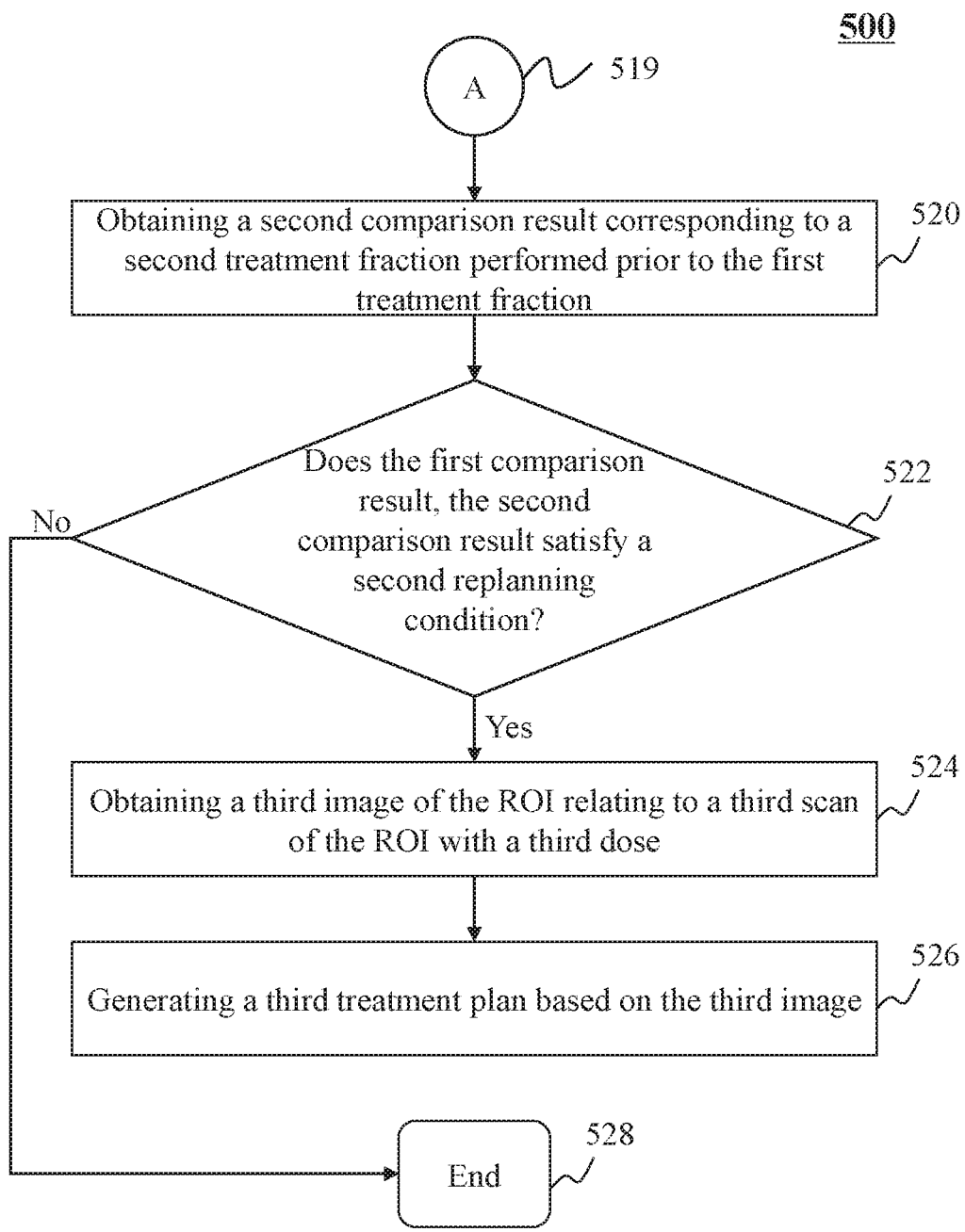
FIG. 5-B

SYSTEM AND METHOD FOR PRETREATEMENT IMAGING IN ADAPTIVE RADIATION THERAPY

TECHNICAL FIELD

The present disclosure generally relates to systems and methods for radiation therapy, and more particularly, to systems and methods for adapting a radiation therapy treatment plan based on pretreatment imaging.

BACKGROUND

Radiation therapy is widely used in cancer therapy and is also indicated for several other health conditions. Conventionally, a radiation therapy treatment plan (also referred herein as a treatment plan) for a cancer patient is generated before treatment starts. The treatment plan may be delivered to the patient during several treatment fractions, spread over a treatment period of multiple days. However, during the treatment period, the anatomy of the tumor or other tissues (e.g., tissue surrounding the tumor) may change. For example, the tumor may grow, deform, or shrink. Accordingly, the treatment plan may need to be updated. Thus, it may be desirable to develop systems and methods for adapting a treatment plan during the course of the treatment period.

SUMMARY

In a first aspect of the present disclosure, a system for adapting treatment plan is provided. The system may include one or more scanners, at least one storage medium including a set of instructions for adapting treatment plan, and at least one processor configured to communicate with the at least one storage medium. When executing the set of instructions, the system may be directed to perform following operations. A planning image of a region of interest relating to a first treatment plan may be obtained. A first image of the region of interest relating to a first scan of the region of interest with a first dose level may be obtained. The planning image may be compared with the first image to generate a first comparison result. The system may determine whether the first comparison result satisfies a first replanning condition. The system may cause, in response to a determination that the first comparison result satisfies the first replanning condition, the one or more scanners to perform a second scan with a second dose level to provide a second image. A second treatment plan may be generated according to the second image, wherein the second dose level may be higher than the first dose level.

In some embodiments, the system may send an instruction to a radiation treatment device to deliver the second treatment plan to the region of interest.

In some embodiments, the first scan may be a cone beam computed tomography (CBCT) scan, and the second scan may be a multislice computed tomography (MSCT) scan.

In some embodiments, to compare the planning image with the first image, the system may be further directed to perform following operations. At least one first value with respect to at least one metric based on the planning image may be determined. At least one second value with respect to the at least one metric based on the first image may be determined. The at least one first value may be compared with the at least one second value.

In some embodiments, to determine whether the first comparison result satisfies the first replanning condition, the system may be further directed to determine whether a difference between the first value and the second value exceeds a threshold.

In some embodiments, the at least one metric may be associated with an anatomical feature in the region of interest.

In some embodiments, the system ay be further directed to send, in response to a determination that the first comparison result fails to satisfy the first replanning condition, an instruction to the radiation treatment device to deliver the first treatment plan to the region of interest.

In some embodiments, to compare the planning image with the first image, the system may be further directed to perform following operations. At least one second comparison result of at least one second treatment fraction performed prior to the first treatment fraction may be obtained. Based on the first comparison result and the at least one second comparison result, whether a second replanning condition is satisfied may be determined. In response to the determination that the second replanning condition is satisfied, a third image relating to a third scan of the region of interest may be obtained. A third treatment plan may be determined based on the third image. In some embodiments, the third scan is an MSCT scan with a third dose level greater than the first dose level.

In some embodiments, the treatment plan includes a plurality of treatment fractions, and the system may be further directed to perform following operations. Whether the first comparison result satisfies a third replanning condition may be determined. In response to the determination that the first comparison result satisfies the third replanning condition, a fourth image relating to a fourth scan of the region of interest may be obtained. A fourth treatment plan may be determined based on the fourth image. In some embodiments, the fourth scan may be an MSCT scan with a fourth dose level greater than the first dose level.

In some embodiments, the first and second scan may be multislice computed tomography (MSCT) scans.

In some embodiments, the first image or the second image may be an MSCT image obtained by a MSCT scanner, and MSCT imaging bore of the MSCT scanner may share a common axis of rotation with a bore of a radiation treatment device.

In a second aspect of the present disclosure, a method for adapting treatment plan is provided. The method may include following operations. A planning image of a region of interest relating to a first treatment plan may be obtained. A first image of the region of interest relating to a first scan of the region of interest with a first dose level may be obtained. The planning image may be compared with the first image to generate a first comparison result. Whether the first comparison result satisfies a first replanning condition may be determined. The method may include causing, in response to a determination that the first comparison result satisfies the first replanning condition, the one or more scanners to perform a second scan with a second dose level to provide a second image. A second treatment plan may be generated according to the second image, wherein the second dose level may be higher than the first dose level.

In some embodiments, an instruction may be sent to a radiation treatment device to deliver the second treatment plan to the region of interest.

In some embodiments, the first scan may be a cone beam computed tomography (CBCT) scan, and the second scan may be a multislice computed tomography (MSCT) scan.

In some embodiments, to compare the planning image with the first image, the method may further include following operations. At least one first value with respect to at least one metric based on the planning image may be determined. At least one second value with respect to the at least one metric based on the first image may be determined. The at least one first value may be compared with the at least one second value.

In some embodiments, to determine whether the first comparison result satisfies the first replanning condition, the method may further including determine whether a difference between the first value and the second value exceeds a threshold.

In some embodiments, the at least one metric may be associated with an anatomical feature in the region of interest.

In some embodiments, the method may further including sending, in response to a determination that the first comparison result fails to satisfy the first replanning condition, an instruction to the radiation treatment device to deliver the first treatment plan to the region of interest.

In some embodiments, to compare the planning image with the first image, the method may further include following operations. At least one second comparison result of at least one second treatment fraction performed prior to the first treatment fraction may be obtained. Based on the first comparison result and the at least one second comparison result, whether a second replanning condition is satisfied may be determined. In response to the determination that the second replanning condition is satisfied, a third image relating to a third scan of the region of interest may be obtained. A third treatment plan may be determined based on the third image. In some embodiments, the third scan is an MSCT scan with a third dose level greater than the first dose level.

In some embodiments, the treatment plan includes a plurality of treatment fractions, and the method may further include following operations. Whether the first comparison result satisfies a third replanning condition may be determined. In response to the determination that the first comparison result satisfies the third replanning condition, a fourth image relating to a fourth scan of the region of interest may be obtained. A fourth treatment plan may be determined based on the fourth image. In some embodiments, the fourth scan may be an MSCT scan with a fourth dose level greater than the first dose level.

In some embodiments, the first and second scan may be multislice computed tomography (MSCT) scans.

In some embodiments, the first image or the second image may be an MSCT image obtained by a MSCT scanner, and MSCT imaging bore of the MSCT scanner may share a common axis of rotation with a bore of a radiation treatment device.

In a third aspect of the present disclosure, a non-transitory computer readable medium is provided. The non-transitory computer readable medium may include executable instructions. When at least one processor executes the instructions, the at least one processor may effectuate a method including one or more of the following operations. A planning image of a region of interest relating to a first treatment plan may be obtained. A first image of the region of interest relating to a first scan of the region of interest with a first dose level may be obtained. The planning image may be compared with the first image to generate a first comparison result. Whether the first comparison result satisfies a first replanning condition may be determined. The method may include causing, in response to a determination that the first comparison result satisfies the first replanning condition, the one or more scanners to perform a second scan with a second dose level to provide a second image. A second treatment plan may be generated according to the second image, wherein the second dose level may be higher than the first dose level.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIGS. 5-A and 5-B are flowcharts illustrating an exemplary process for adapting a radiation therapy treatment plan according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by other expression if they may achieve the same purpose.

Figure 2:
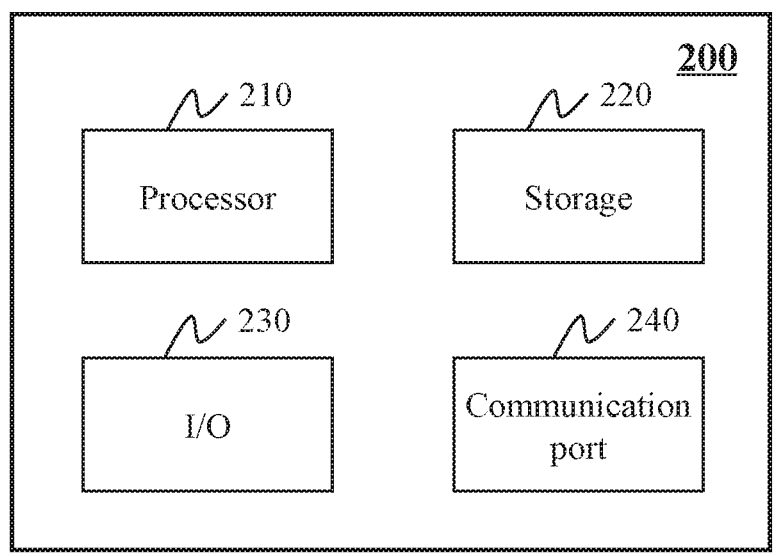
FIG. 2 is a schematic diagram illustrating hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an erasable programmable read-only memory (EPROM). It will be further appreciated that hardware modules/units/ blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include" and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

Provided herein are systems and components for non-invasive imaging and/or treatment, such as for disease diagnosis, treatment or research purposes. In some embodiments, the system ay be a radiation therapy system, a computed tomography (CT) system, an emission computed tomography (ECT) system, an X-ray photography system, a positron emission tomography (PET) system, or the like, or any combination thereof. For illustration purposes, the disclosure describes systems and methods for radiation therapy. The term "image" used in this disclosure may refer to a 2D image, a 3D image, or a 4D image. In some embodiments, the term "image" may refer to image of a region of interest (ROI) of a patient. The term "region of interest" or "ROI" used in this disclosure may refer to a part of an image along a line, in two spatial dimensions, in three spatial dimensions, or any of the proceeding as they evolve as a function of time. The image may be a CT image, an EPID (Electronic Portal Image Device) image, a fluoroscopy image, an ultrasound image, a PET image or an MRI image. The term "planning image" used in this disclosure may refer to an image according to which a treatment plan is made. The term "treatment plan" in this disclosure may include a set of parameters describing how the radiation is delivered to the patient, including but not limited to beam aperture size, radiation dose level distribution, radiation duration, and position of radiation target of the patient. The planning image may be used to identify radiotherapy targets, organs at risk, and patient external contour (e.g., skin). Tissue attenuation values yielded by the planning image may be converted to electron densities and are used to perform radiation dose level calculation. The treatment plan may include one or more treatment fractions. For each of the treatment fraction, the radiation treatment plan may include a plurality of treatment parameters, such as a planned fraction duration, a planned radiation dose level, a planned radiation energy delivery direction, a planned radiation energy beam shape, a planned radiation beam cross-sectional area, a planned region of interest (ROI), etc.

The term "guiding image" used in this disclosure may include an image taken during or before the radiation therapy to guide radiation delivery. The guiding image may include a low dose level guiding image for determining radiotherapy target position, and a high dose level guiding image for adapting the treatment plan during or before the radiotherapy.

The term "image data" used in this disclosure may refer to radiation data (e.g., CT data) and projection data corresponding to the radiation data. This is not intended to limit the scope the present disclosure. For persons having ordinary skills in the art, a certain number of variations, changes, and/or modifications may be deduced under the guidance of the present disclosure. Those variations, changes, and/or modifications do not depart from the scope of the present disclosure.

Before a patient receives radiation therapy (e.g., days before or weeks before), the planning image may be taken, and a treatment plan may be designed for the patient based on the planning image. A guide image may be taken to guide radiation delivery during or before the radiation therapy (e.g., on the day of treatment, or hours before the treatment, or minutes before the treatment, or seconds before the treatment, or during the treatment). However, radiotherapy targets, organs at risk, and patient external contour may change during or before the radiation therapy, and thus, the treatment plan may need to be modified in real time to accommodate the changes. As adapting of the treatment plan during or before the radiation therapy is uncertain, the patient may be at risk of exposure to unnecessary radiation. For example, if the treatment plan does not need to be modified in real time, a patient may suffer unnecessary radiation dose level if a high dose level guiding image is taken during the radiation therapy. As another example, if the treatment plan needs to be modified in real time, a low dose level guiding image may be not precise enough to modify the treatment plan, therefore causing the deviation of the radiation delivery. Thus, an aspect of the present disclosure relates to systems and methods for adapting guiding image dose level based on images acquired before or during a treatment.

In this disclosure, before the treatment plan is prescribed, a planning image of the treatment plan regarding a subject may be obtained. During or before the radiation therapy (e.g., on the day of treatment, or hours before the treatment, or minutes before the treatment, or seconds before the treatment), a CT scan of a first dose level may be performed to generate a first image (e.g., a low dose level guiding image). A decision may be made as to whether a high dose level guiding image is needed during or before the treatment based on the planning image and the first image by comparing anatomical information of the two images. Demand for a high dose level guiding image may be triggered when the comparison of anatomical information indicates a significant change of anatomical information indicated by, for example, a difference between the anatomical information being greater than a threshold. In response to the determination that the high dose level guiding image is needed, a CT scan of a second dose level may be performed to generate a second image (e.g., a high dose level guiding image). A second treatment plan may be generated based on the second image. The first dose level may be lower than the second dose level. As such, the treatment plan may be adapted timely and accurately if the treatment plan needs to be modified, and a patient may not suffer unnecessary radiation dose level if the treatment plan does not need to be modified. In functional imaging modalities (e.g., positron emission tomography (PET), or contrast-enhanced CT, etc.), the same argument applies to changes of physiological parameters. For example, a planning PET image is taken with a physiological parameter, e.g., a first tracer concentration level, before the radiation therapy. If a first PET image, obtained during or before the radiation therapy, indicates that this physiological parameter has changed beyond a threshold, then a second PET image, of which tracer concentration level is higher than that of the planning PET image may be taken for replanning, using the same or another tracer compound.

Figure 1:
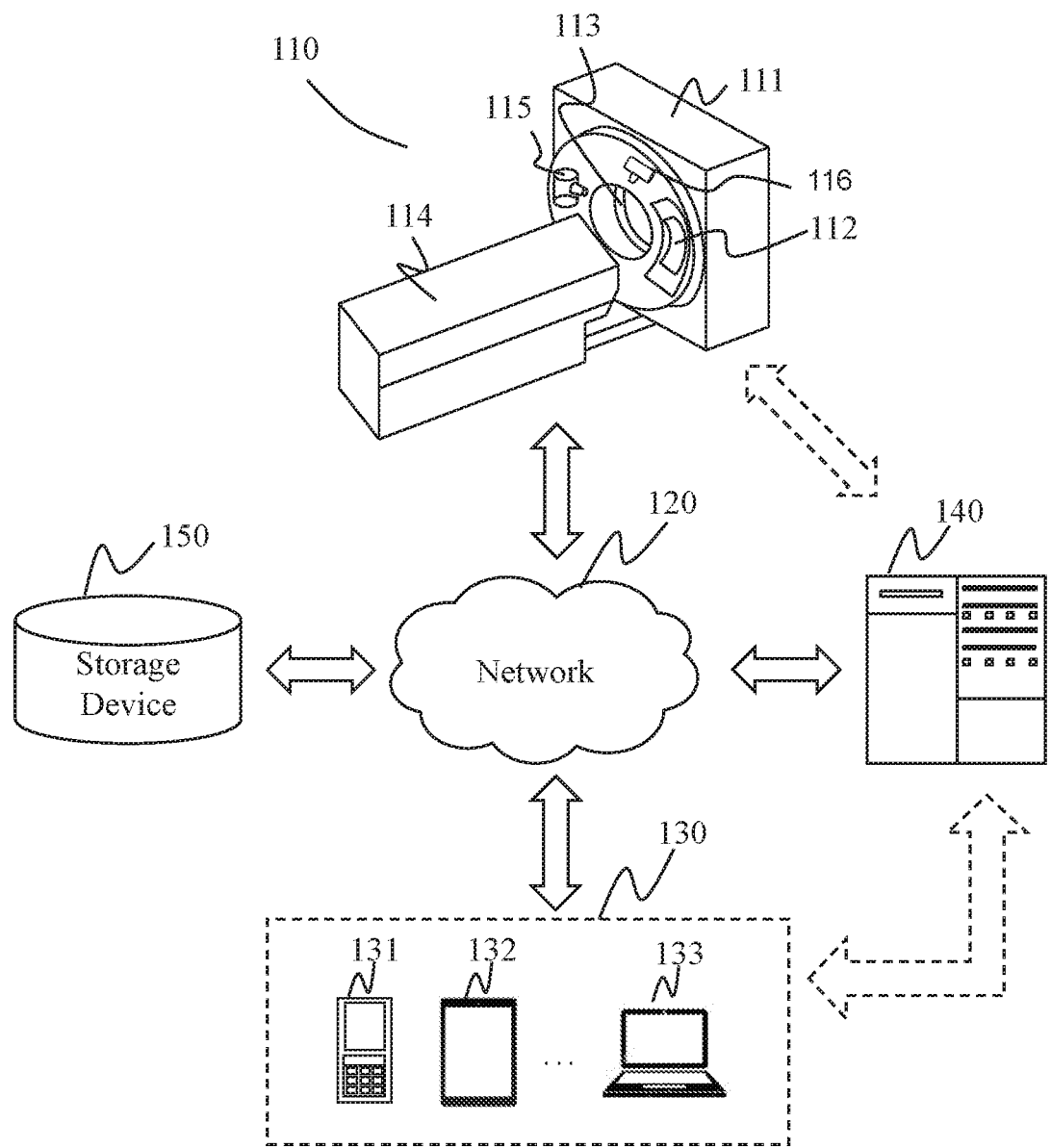
FIG. 1 is a schematic diagram illustrating an exemplary radiation therapy system according to some embodiments of the present disclosure.

FIG. 1 is a schematic diagram illustrating an exemplary radiation therapy system 100 according to some embodiments of the present disclosure. The radiation therapy system 100 may include an image-guided treatment apparatus 110, a network 120, one or more terminals 130, a processing device 140, and a storage device 150.

The image-guided treatment apparatus 110 may include an imaging component, a treatment component, a gantry 111, a table 114, an imaged region 113, or the like. The imaging component may include an imaging-radiation source 115, a detector 112, or the like. The treatment component may include a treatment radiation source 116, an accelerator (not shown in FIG. 1), or the like. The gantry 111 may be configured to accommodate the imaging component and the treatment component, such as the imaging-radiation source 115, the detector 112, and the treatment radiation source 116. A subject may be placed on the table 114 for treatment and/or scan.

The imaging component may generate an image of the subject before, during and/or after a treatment fraction. The imaging component may include a computed tomography (CT) component, an ultrasound imaging component, a fluoroscopy imaging component, a magnetic resonance imaging (MRI) component, a single photon emission computed tomography (SPECT) component, a positron emission tomography (PET) component, or the like, or any combination thereof.

The imaging-radiation source 115 may emit radiation toward the subject. The detector 112 may detect radiation events (e.g., x-ray photons, gamma-ray photons) emitted from the imaged region 113. In some embodiments, the detector 112 may include one or more detector units. The detector units may include a scintillation detector (e.g., a cesium iodide detector, a gadolinium oxysulfide detector), a gas detector, etc. The detector unit may include a single-row detector and/or a multi-rows detector.

In some embodiments, the imaging component may be a CBCT imaging component. The CBCT imaging component may perform a CBCT scan on the subject by emitting cone beam X-rays to the subject. In some embodiments, the imaging component may be a multi-slice CT (MSCT) imaging component. The MSCT imaging component may perform an MSCT scan of the subject. In some embodiments, the imaging component may be an integrated. CT imaging component that can perform a CBCT scan and an MSCT scan. An MSCT scan is comprised of one or more axial slices of the imaged object (usually the patient, or human or animal subject).

The treatment component may deliver radiation treatment to the subject. The treatment radiation source 116 may emit treatment radiations towards the subject. The therapy radiations may be accelerated by, for example, an accelerator (not shown in FIG. 1) and irradiate on the subject.

In some embodiments, the image-guided treatment apparatus 110 may include two gantries that house the imaging component and the treatment component, respectively. The imaging component (e.g., the imaging-radiation source 115 and the detector 112) and the corresponding gantry may be spaced by a distance from the treatment component (e.g., the treatment radiation source 116) and the corresponding gantry. In some embodiments, the corresponding gantry of the imaging component and the corresponding gantry of the imaging component may have collinear bore. For example, bore of the imaging component gantry and bore of the treatment component gantry may share an axis of rotation. The subject may be positioned in different positions in the table 114 for imaging and treatment. In some embodiments, the imaging-radiation source 115 and the treatment radiation source 116 may be integrated as one radiation source to image and/or treat the subject.

In some embodiments, the radiation therapy system 100 may include a radiation treatment device, and a CT scanner. Such device is described in US publication No. 20170189720A1 entitled as "radiation therapy system", US publication No. 20170189719A1 entitled as "radiation therapy positioning system", and US publication No. 20170189724A1 entitled as "radiation therapy system", and the contents of these applications are referenced herein and incorporated into this application. The radiation treatment device may include one or more components that is the same as or substantially similar to those of the image-guided treatment apparatus 110. For example, the radiation treatment device may include the same components as the image-guided treatment apparatus 110. As another example, the radiation treatment device may include a treatment component, a gantry, a table, and a detecting region.

In some embodiments, the CT scanner may be a CBCT scanner and/or an MSCT scanner. The CBCT scanner may perform a CBCT scan of a subject. The MSCT scanner may perform an MSCT scan of a subject. The images generated based on the CBCT scan or the MSCT scan may be stored in a storage device in the radiation therapy system 100 for adaptive radiation therapy planning. The CBCT scanner or the MSCT scanner may include one or more components of a CT scanner known to a person of ordinary skill in the art. For example, the CBCT scanner may include a gantry, a detector, a detecting region, a table, and a CBCT radiation-emitting scanning source.

Merely by way of example, the radiation therapy system 100 may include an MSCT scanner and a radiation treatment device including a CBCT imaging component and a treatment component. The MSCT scanner may perform an MSCT scan of a subject. The radiation treatment device including the CBCT imaging component and the treatment component may perform a CBCT scan and/or treat the subject. Additionally or alternatively, the radiation therapy system 100 may include a CBCT scanner and a radiation treatment device including an MSCT imaging component and a treatment component. Bore of the MSCT imaging component may share an axis of rotation with the treatment component.

The network 120 may include any suitable network that can facilitate the exchange of information and/or data for the radiation therapy system 100. In some embodiments, one or more components of the radiation therapy system 100 (e.g., the image-guided treatment apparatus 110, the terminal 130, the processing device 140, the storage device 150, etc.) may communicate information and/or data with one or more other components of the radiation therapy system 100 via the network 120. For example, the processing device 140 may obtain image data from the image-guided treatment apparatus 110 via the network 120. As another example, the processing device 140 may obtain user instructions from the terminal 130 via the network 120. The network 120 may be and/or include a public network (e.g., the Internet), a private network (e.g., a local area network (LAN), a wide area network (WAN))), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NEC) network, or the like, or any combination thereof. In some embodiments, the network 120 may include one or more network access points. For example, the network 120 may include wired and/or wireless network access points such as base stations and/or internet exchange points through which one or more components of the radiation therapy system 100 may be connected to the network 120 to exchange data and/or information.

Figure 3:
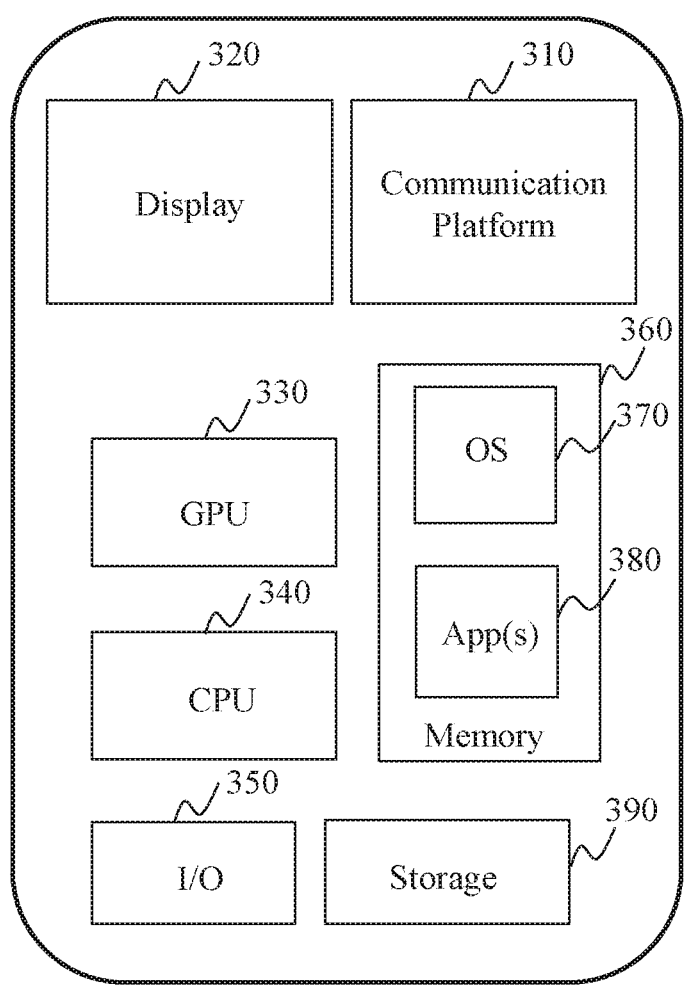
FIG. 3 is a schematic diagram illustrating hardware and/or software components of an exemplary mobile device according to some embodiments of the present disclosure.

The terminal(s) 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. Merely by way of example, the terminal 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process data and/or information obtained from the image-guided treatment apparatus 110, the terminal 130, and/or the storage device 150. In some embodiments, the processing device 140 may be a single server or a server group. The server group may be centralized or distributed. In some embodiments, the processing device 140 may be local or remote. For example, the processing device 140 may access information and/or data stored in the image-guided treatment apparatus 110, the terminal 130, and/or the storage device 150 via the network 120. As another example, the processing device 140 may be directly connected to the image-guided treatment apparatus 110, the terminal 130 and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage, removable storage, a volatile read-and-write memory, a read-only memory (ROM), or the like, or any combination thereof. Exemplary mass storage include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components of the radiation therapy system 100 (e.g., the processing device 140, the terminal 130). One or more components of the radiation therapy system 100 may access the data or instructions stored in the storage device 150 via the network 120. In some embodiments, the storage device 150 may be directly connected to or communicate with one or more other components of the radiation therapy system 100 (e.g., the processing device 140, the terminal 130). In some embodiments, the storage device 150 may be part of the processing device 140.

FIG. 2 is a schematic diagram illustrating exemplary hardware and/or software components of an exemplary computing device 200 on which the processing device 140 may be implemented according to some embodiments of the present disclosure. As illustrated in FIG. 2, the computing device 200 may include a processor 210, storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process image data obtained from the image-guided treatment apparatus 110, the terminal 130, the storage device 150, and/or any other component of the radiation therapy system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is illustrated in the computing device 200 in FIG. 2. However, it should be noted that the computing device 200 in the present disclosure may also include multiple processors, and thus operations and/or method steps that are performed by one processor as described in the present disclosure may also be jointly or separately performed by the multiple processors. For example, if in the present disclosure the processor of the computing device 200 executes both operations A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the image-guided treatment apparatus 110, the terminal 130, the storage device 150, and/or any other component of the radiation therapy system 100. In some embodiments, the storage 220 may include a mass storage, removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure.

The I/O 230 may input and/or output signals, data, information, etc. In some embodiments, the I/O 230 may enable a user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the image-guided treatment apparatus 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device 300 on which the terminal 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the radiation therapy system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
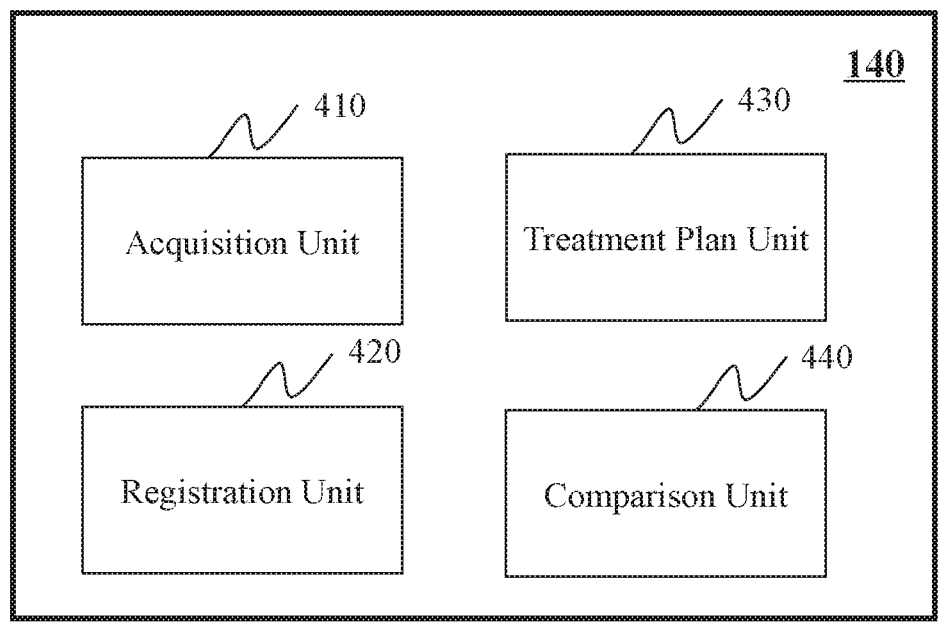
FIG. 4 is a block diagram illustrating an exemplary processing engine according to some embodiments of the present disclosure.

FIG. 4 is a block diagram illustrating an exemplary processing device 140 according to some embodiments of the present disclosure. The processing device 140 may include an acquisition unit 410, a registration unit 420, a treatment plan unit 430, and a comparison unit 440. The processing device 140 may be implemented on various components (e.g., the processor 210 of the computing device 200 as illustrated in FIG. 2).

The acquisition unit 410 may obtain one or more images related to an ROI of a patient. The one or more images may include a planning image and/or a guiding image. For example, the acquisition unit 410 may obtain a planning image of a region of interest (ROI) relating to a treatment fraction of a treatment plan. As another example, the acquisition unit 410 may obtain a guiding image of the ROI produced by a scan, such as a CBCT scan and/or an MSCT scan. The acquisition unit 410 may obtain the one or more images from a storage device in the radiation therapy system 100, such as the storage device 150.

The registration unit 420 may correct setup error between a guiding image and a planning image. The setup error may describe discrepancy between an intended treatment position where the planning image is taken and an actual treatment position where the guiding image is taken. For example, the registration unit 420 may register a guiding image produced by a CBCT scan with a planning image relating to a treatment plan. The registration unit 420 may perform the image registration based on any suitable image registration techniques including, for example, a voxel-based registration technique, a landmark-based registration technique, a segmentation-based registration technique, or the like, or a combination thereof. In some embodiments, registration unit 420 may perform a rigid image registration.

The treatment plan unit 430 may obtain and/or generate a treatment plan. In some embodiments, the treatment plan unit 430 may generate a treatment plan based on an image, such as a planning image taken before treatment, a guiding image (e.g., a high dose level guiding image). The treatment plan generated by the treatment plan unit 430 may include one or more treatment fractions. For each of the treatment fraction, the treatment plan may include a plurality of treatment parameters, such as a planned fraction duration, a planned radiation dose level, a planned radiation energy delivery direction, a planned radiation energy beam shape, a planned radiation beam cross-sectional area, a planned region of interest (ROI), etc. Additionally or alternatively, the treatment plan unit 430 may send an instruction to a radiation treatment device to deliver a treatment based on the treatment plan.

The comparison unit 440 may determine and/or obtain a compare result of two or more images. In some embodiments, the comparison unit 440 may compare anatomy information of two images to generate a comparison result of the two images. For example, the comparison unit 440 may determine a first value of a metric based on a first image and a second value of the metric based on a second image. The comparison unit 440 may then compare the first value with the second value by way of, e.g., determining a difference between the first value and the second value. The metric may include any suitable metric relating to a parameter or characteristic of an anatomical feature in the first image and/or the second image. The anatomical feature may include a malignant tissue (e.g., a tumor, or a cancer-ridden organ) or other tissue (e.g., a tissue surrounding the malignant tissue). The metric may include the location of the anatomical feature, the shape of the anatomical feature, the density of the anatomical feature, the volume of the anatomical feature, an attenuation value of the anatomical feature, or the like, or any combination thereof. The difference between the first value and the second value of the metric may be designated as the comparison result of the two images by the comparison unit 440.

In some embodiments, the registration unit 420 may register an image produced by a CBCT scan to a planning image relating to a first treatment fraction of a treatment plan. The comparison unit 440 may compare a planning image with a registered image to generate a first comparison result. Additionally or alternatively, the comparison unit 440 may make a determination as to whether the first comparison result satisfies a first replanning condition to identify a need for replanning. In some embodiments, the comparison unit 440 may make a determination as to whether the first comparison result and a second comparison result corresponding to a second treatment fraction performed prior to the first treatment fraction satisfy a second replanning condition to identify a need for replanning.

It should be noted that the above descriptions of the processing device 140 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the processing device 140 may include one or more other modules. In some embodiments, two or more units in the processing device 140 may form one module. However, those variations and modifications also fall within the scope of the present disclosure.

FIGS. 5-A and 5-B illustrate a flowchart illustrating an exemplary process for adapting guiding image dose level according to some embodiments of the present disclosure. In some embodiments, at least part of process 500 may be performed by the processing device 140 (implemented in, for example, the computing device 200 shown in FIG. 2).

The radiation therapy may be a photon-based radiation therapy, a brachy therapy, an electron beam therapy, a proton therapy, a neutron therapy, a particle therapy, or other types of therapies. In some embodiments, the treatment plan may include a plurality of treatment fractions. At least part of the process 500 may be performed before one or more treatment fractions of the plurality of the treatment fractions. In some embodiments, the treatment plan may include a single treatment fraction. At least part of the process 500 may be performed before the single treatment fraction. Merely by way of example, operations illustrated in FIG. 5A may be performed before the single treatment fraction.

In 502, a planning image of a region of interest (ROI) relating to a first treatment fraction of a first treatment plan may be obtained. In some embodiments, 502 may be performed by the acquisition unit 410. In some embodiments, the planning image may be obtained from a storage device in the radiation therapy system 100, such as the storage device 150.

The first treatment plan may include a plurality of treatment fractions. The first treatment fraction may be any treatment fraction of the plurality of the treatment fractions. As used herein, a first treatment fraction is used to refer to a treatment fraction to be performed with respect to which an assessment is made as to whether the treatment plan needs to be revised. A treatment fraction performed prior to a first treatment fraction may be referred to as a prior treatment fraction or a second treatment fraction. For instance, between a first treatment fraction and a second treatment fraction, the first treatment fraction is performed subsequent to the second treatment fraction. The ROI may be a region of a patient including at least part of a malignant tissue (e.g., a tumor, a cancer-ridden organ, or non-cancerous target of radiation therapy). Additionally or alternatively, the ROI may include other tissue, such as a tissue surrounding the malignant tissue. In some embodiments, the planning image of the ROI acquired before the first treatment fraction is performed by an imaging acquisition device (e.g., the image-guided treatment apparatus 110 including an imaging component, a CT scanner). The first treatment plan may be generated based on the planning image and stored in the storage device (the storage device 150).

Additionally or alternatively, the first treatment plan may include a plurality of first treatment parameters for each treatment fraction. The first treatment parameters of a treatment fraction may include a first planned fraction duration, a first planned radiation dose level, a first planned radiation energy delivery direction, a first planned radiation energy beam shape, a first planned radiation beam cross-sectional area, or the like, or any combination thereof.

In 504, the acquisition unit 410 may obtain a first image of the ROI produced by a first scan of the ROI. The first scan may be performed with a first dose level. In some embodiments, the first image may be a low dose level guiding image. In some embodiments, the acquisition unit 410 may obtain the first image from a storage device in the radiation therapy system 100, such as the storage device 150.

In some embodiments, the first scan may be a CBCT scan with the first dose level performed by a CBCT scanner and/or an imaging component of the image-guided treatment apparatus 110. For example, the imaging component of the image-guided treatment apparatus 110 may be a CBCT imaging component as described in connection with FIG. 1. The imaging-radiation source 115 may perform scanning by emitting one or more cone beam X-rays. The radiation dose level of the core beam X-rays may be equal to the first dose level. Additionally or alternatively, the first scan may be performed by a CBCT scanner in the radiation therapy system 100 (not shown in FIG. 1).

The first dose level may be any suitable value for a CBCT scan. In some embodiments, the first dose level may be selected based on the position of the ROI (e.g., a tumor, an organ at risk). The first dose level for different ROIs at different positions may be different from each other. Merely by way of example, the first dose level for an ROI in the head may range from 0.5 mGy to 6 mGy. In some embodiments, the first scan may be an MSCT scan with the first dose level performed by an MSCT scanner and/or an imaging component of the image-guided treatment apparatus 110.

The first image may be generated based on image data acquired from the first scan. One or more components (e.g., the process device 140) may process the image data to provide the first image. The first image and/or the corresponding image data may be stored in a storage device (e.g., the storage device 150). For example, the processing device 140 may process and/or reconstruct the first image based the image data acquired from the first scan, and transmit it to the storage device 150.

To perform the first scan of a subject based on the planning image, one or more tattoos and/or makers may be marked on the skin of the subject by, for example, a doctor, an imaging specialist, etc., to identify a target treatment area before treatment. In the first scan, the subject may be placed, based on the one or more tattoos and/or markers, at the same (or essentially the same) position as that when the planning image was taken.

In 506, the first image may be registered with the planning image to generate a registered first image. In some embodiments, 506 may be performed by the registration unit 420. The registration may be performed based on any suitable image registration techniques including, for example, a voxel-based registration technique, a landmark-based registration technique, a segmentation-based registration technique, or the like, or a combination thereof. In some embodiments, the registration may be a rigid registration. In some embodiments, the registration may be a non-rigid deformable registration.

Merely by way of example, the first image may be registered with the planning image based the landmark-based registration technique. The landmark for registration may be a visible anatomical point that can be identified and located. For example, the landmark may be a bone. In the registration, the registration unit 420 may align a landmark in the planning image with a corresponding landmark in the first image. The registration of the first image with the planning image may be performed to remove at least part of an error due to, for example, the misalignment of the subject when the first image is acquired compared to when the planning image was acquired. The misalignment may be caused by, for example, a weight change of the subject, an error in the setup of the subject for the acquisition of the first image, or the like, or a combination thereof.

In 508, the planning image may be compared with the registered first image to generate a first comparison result. In some embodiments, 508 may be performed by the comparison unit 440. In some embodiments, the planning image may be compared with the first image to generate a first comparison result. To compare the planning image with the registered first image (or the first image), the anatomy information in the planning image and the registered first image (or the first image) may be compared. For example, the comparison unit 440 may determine a first value of a metric based on the planning image and a second value of the metric based on the registered first image (or the first image). The comparison unit 440 may then compare the first value with the second value by way of, e.g., determining a difference between the first value and the second value. The difference between the first value and the second value of the metric may be designated as the first comparison result by the comparison unit 440.

The metric may include any suitable metric relating to a parameter or characteristic of an anatomical feature in the planning image and/or the registered first image (or the first image). The anatomical feature in the planning image and/or the registered first image (or the first image) may include a malignant tissue (e.g., a tumor, or a cancer-ridden organ, or a non-cancerous target of radiation therapy) or other tissue (e.g., a tissue surrounding the malignant tissue) as described in connection with 502. The metric may include the location of the anatomical feature, the shape of the anatomical feature, the density of the anatomical feature, the volume of the anatomical feature, an attenuation value of the anatomical feature, or the like, or any combination thereof. Additionally or alternatively, the metric may include any other suitable metric relating to the planning image and/or the registered first image (or the first image), such as a volume of the image. For instance, a sum of a whole image of a subject, including air, may be determined to provide the volume of the imaged anatomy, which may serve as an indicator of the weight change of the subject. For another example, volume of voxels containing fat may be determined to serve as an indicator of the weight change of the subject.

In 510, a determination may be made as to whether the first comparison result satisfies a first replanning condition. In some embodiments, 510 may be performed by the comparison unit 440. The first replanning condition may be a default condition retrieved from a storage device (e.g., the storage device 150) in the radiation therapy system 100 or be set by a user via the one or more terminals 130. In response to the determination that the first replanning condition is satisfied, 512 may be performed. Otherwise, 518 may be performed.

As described in connection with 508, the first comparison result of the planning image and the registered first image (or the first image) may include a difference with respect to a metric between a first value associated with the planning image and a second value associated with the registered first image (or the first image). The first replanning condition may include a replanning threshold. According to the first replanning condition, when the difference exceeds the replanning threshold, a deviation in the anatomical feature of the subject from the planning image is determined to have exceeded a tolerable range and thus, a replanning is recommended. The replanning threshold may be a default value retrieved from a storage device (e.g., the storage device 150) or be set by a user via the one or more terminals 130. Additionally or alternatively, the replanning threshold may be determined by a component of the radiation therapy system 100, such as the comparison unit 440.

For illustration purposes, the present disclosure takes a density of the malignant tissue as an example. In some embodiments, the replanning threshold of the density of the malignant tissue may be 0.01 g/cm$^3$. The corresponding first replanning condition may be that the difference between a first density of the malignant tissue in the planning image and a second density of the malignant tissue exceeds 0.01 g/cm$^3$. In some embodiments, the replanning threshold regarding the density of the malignant tissue may be 0.1% of the first density of the malignant tissue in the planning image. The corresponding replanning condition may be that the difference between the first density of the malignant tissue and the second density of the malignant tissue exceeds 0.1% of the first density of the malignant tissue. It should be noted that the above descriptions are provided for the purposes of illustration, and not intended to limit the scope of the present disclosure. The replanning threshold corresponding to the density of a malignant tissue may be any suitable value. The first replanning condition may be based on a metric other than the density of the malignant tissue. In some embodiments, dual energy CT may be used to detect small changes in the attenuating characteristics of the anatomy.

In some embodiments, in 508, a plurality of metrics of the planning image and the registered first image (or the first image) may be compared. The first comparison result may include a difference between first value and second value for each metric. The first replanning condition may include a plurality of sub-replanning conditions corresponding to the plurality of metrics. The first replanning condition may be satisfied when at least part of the sub-replanning conditions is satisfied.

In 512, a second image of the ROI relating to a second scan of the ROI may be obtained. In some embodiments, 512 may be performed by the acquisition unit 410. The second scan may be performed with a second dose level. In some embodiments, the second scan may be an MSCT scan with the second dose level performed by an MSCT scanner and/or an MSCT imaging component of the image-guided treatment apparatus 110. The second image may be generated based on image data acquired from the second scan. The second scan may be reconstructed based on combined data obtained during the first and second scan, in the case where the first and second images are obtained using the same imaging and patient configuration. One or more components (e.g., the processing device 140) may process the image data to provide the second image. The second image and/or the corresponding image data may be stored in a storage device (e.g., the storage device 150). Operations 512 and 504 may be performed in a substantially similar manner.

The second dose level may be any suitable value for an MSCT scan equal to or greater than the first dose level. In some embodiments, the second dose level may be selected based on the position of the ROI (e.g., a tumor, an organ at risk). The second dose level for different ROIs at different positions may be different from each other. Merely by way of example, the second dose level for an ROI in the head may range from 8.7 mGy to 40.0 mGy.

In 514, a second treatment plan may be generated based on the second image. In some embodiments, 514 may be performed by the treatment plan unit 430. Additionally or alternatively, at least part of the second treatment plan may be generated based on an instruction of a user (e.g., a doctor, a clinician). Merely by way of example, a clinician may input a desired value or range of a radiation treatment parameter (e.g., a radiation dose level) based on the second image via the one or more terminals 130. The second treatment plan may be generated by the radiation therapy system 100 according to or taking into consideration of the clinician's input.

The second treatment plan may include one or more treatment fractions. In some embodiments, the second treatment plan may include the same number of treatment fractions as the first treatment plan. In some embodiments, the second treatment plan may include more or fewer treatment fractions than the first treatment plan. For a treatment fraction, the second treatment plan may include a plurality of second treatment parameters, such as a second planned fraction duration, a second planned radiation dose level, a second planned radiation energy delivery direction, a second planned radiation energy beam shape, a second planned radiation beam cross-sectional area.

In 516, an instruction may be sent to the image-guided treatment apparatus 110 to deliver a treatment according to the second treatment plan to the ROI. In some embodiments, 516 may be performed by the treatment plan unit 430. The instruction may include the plurality of second treatment parameters for each treatment fraction in the second treatment plan. The image-guided treatment apparatus 110 may deliver the second treatment plan based on the plurality of second treatment parameters for each treatment fraction. In some embodiments, the instruction may be a real-time instruction according to which a treatment is delivered upon or shortly after (e.g., within minutes, within hours, one the same day, etc.) the instruction is generated. The real-time instruction may cause the image-guided treatment apparatus 110 to immediately or substantially immediately process the instruction and deliver a treatment to the subject. In some embodiments, an instruction may be non-real time for future treatment that is to be delivered, e.g., on the second day, in a few days, etc. The non-real-time instruction may require the image-guided treatment apparatus 110 to process the instruction and deliver a treatment to the subject at a defined time. In some embodiments, an instruction may include a real-time portion and a non-real time portion. For instance, the real-time portion is for immediate or substantially immediate processing and delivery of a treatment fraction to the subject, while the non-real time portion is for the delivery of one or more treatment fractions at one or more defined times in the future.

In 518, in response to the determination that the first replanning condition is not satisfied, an instruction may be sent to the image-guided treatment apparatus 110 to deliver the first treatment plan to the ROI. In some embodiments, 518 may be performed by the treatment plan unit 430. Operations 518 and 516 may be performed in a substantially similar manner.

In some embodiments, process 500 may terminate at 518 and does not proceed to node A 519 and perform at least some of operations starting from node A 519 illustrated in FIG. 5-B. In some embodiments, process 500 may proceed further to 519 and perform at least some of operations starting from node A 519 illustrated in FIG. 5-B. In some embodiments, node A 519 may be performed after 510 is performed. Operation 518 and node A 519 may be performed simultaneously. In some embodiments, in 508, the planning image may be compared with the first image directly to generate a first comparison result, thus operation 506 may be omitted.

In 520, a second comparison result corresponding to a second treatment fraction performed prior to the first treatment fraction may be obtained. In some embodiments, 520 may be performed by the acquisition unit 410. The second comparison result corresponding to the second treatment fraction may be generated in a manner that is the same as or similar to the first comparison result, and stored in a storage device in the radiation therapy system 100. For example, in the second treatment fraction, operations that are the same as or similar to operations 504 to 508 may be performed to generate the second comparison result.

In 522, a determination may be made as to whether a second replanning condition is satisfied based on the first comparison result and the second comparison result. In some embodiments, 522 may be performed by the comparison unit 440. The determination may be made based on the first comparison result, the second comparison result, and the first replanning condition to assess a trend in which the comparison results change during the course of the treatment performed according to the treatment plan(s). The trend, in turn, may serve as an indicator regarding a change of the anatomical feature of a subject. In response to the determination that the second replanning condition is satisfied, 524 may be performed. Otherwise, 528 may be performed.

In some embodiments, a first difference corresponding to the first treatment fraction and a second difference corresponding to the second treatment fraction may be determined. The first difference may be a difference between the first comparison result and the replanning threshold of the first replanning condition. The second difference may be a difference between the second comparison result and the replanning threshold of the first replanning condition.

For illustration purposes, the determination of the first difference is described as an example. As described in connection with 508 and 510, the first comparison result may include a difference with respect to a metric between a first value associated with a planning image and a second value associated with a registered first image (or a first image) acquired by a first scan. The first replanning condition may include a replanning threshold relating to the difference between the first value and the second value of the metric. The first difference may be a difference between the replanning threshold and the first comparison result.

As described elsewhere in the present disclosure, the first difference corresponding to the first treatment fraction and the second difference corresponding to the second treatment fraction may indicate a trend in which comparison results change over the course of the treatment of the subject according to the treatment plan(s). For example, when the first difference is less than the second difference, it may indicate a trend toward the satisfaction of the first replanning condition.

In some embodiments, the second replanning condition may be that the first difference corresponding to the first treatment fraction is less than the second difference corresponding to the second treatment fraction. Additionally or alternatively, the second replanning condition may be that the first difference is less than the second difference, and the difference between the first difference and the second difference is greater than a threshold. The satisfaction of the second replanning condition may indicate that a replanning is needed.

In 524, a third image of the ROI relating to a third scan of the ROI may be obtained. In some embodiments, 524 may be performed by the acquisition unit 410. The third scan may be performed with a third dose level. In some embodiments, the third scan may be an MSCT scan with the third dose level performed by an MSCT scanner and/or an MSCT imaging component of the image-guided treatment apparatus 110. The third dose level may be any suitable value for the MSCT scan greater than the first dose level. In some embodiments, the third dose level may be associated with a position of the ROI (e.g., a tumor, an organ at risk). The third dose level for different ROIs at different positions may be different from each other. Merely by way of example, the third dose level for an ROI in the head may range from 8.7 mGy to 22.0 mGy. Operations 524 and 512 may be performed in a substantially similar manner.

In 526, a third treatment plan may be generated. In some embodiments, 526 may be performed by the treatment plan unit 430. The generation of the third treatment plan may be performed based on the third image, and/or an instruction of a user (e.g., a doctor, a clinician). Operations 526 and 514 may be performed in a substantially similar manner. In some embodiments, the third treatment plan may be generated during the course of radiation delivery according to the first treatment plan (e.g., operation 518). For example, after 510 is performed, operation 518 and node A 519 may be performed simultaneously.

In 528, in response to the determination that the second replanning condition is not satisfied, the process 500 may be ended.

It should be noted that the above descriptions of process 500 are provided for the purposes of illustration, and not intended to limit the scope of the present disclosure. For persons having ordinary skills in the art, various modifications and changes in the forms and details of the application of the above method and system may occur without departing from the principles of the present disclosure. However, those variations and modifications also fall within the scope of the present disclosure.

In some embodiments, one or more operations may be added or omitted. For example, some or all operations of 519 to 528 may be omitted. As another example, operations 524 and 526 may be omitted. In response to the determination that the second replanning condition is satisfied, operations 512 and 514 may be performed to generate the second treatment plan. In some embodiments, in 520, the acquisition unit 410 may obtain a plurality of previous comparison results corresponding to a plurality of prior treatment fractions performed prior the first treatment fraction. The comparison unit 440 may determine whether a second replanning condition is satisfied based on the first comparison result, the plurality of the previous comparison results, and the first replanning condition. The second replanning condition may be satisfied when the previous comparison results and the first comparison result indicate a trend toward satisfaction of the first replanning condition.

In some embodiments, additional operations may be performed after 518, or between 510 and 518, or between 508 and 510, to determine a difference between the first comparison result and the replanning threshold of the first replanning condition as described in connection with 522. The comparison unit 440 may determine whether the difference satisfies a third replanning condition, e.g., the difference being less than a threshold. In response to the determination that the third replanning condition is satisfied, a fourth treatment plan may be generated based on a fourth image of the ROI. The fourth treatment plan may be generated before or during the course of radiation delivery according to the first treatment plan (e.g., operation 518). The fourth image may relate to an MSCT scan with a fourth dose level. The fourth dose level may be equal to or greater a the first dose level. The fourth treatment plan may be generated in a manner substantially similar to the generations of the second treatment plan, and/or the third treatment plan as described in connection with FIGS. 5-A and 5-B.

The various dose levels of the scans described above may be selected independently based on considerations including, for example, the position to be scanned and/or the type of scan to be performed (e.g., relevant description in connection with 510 in FIG. 5-A, 522 in FIG. 5-B, etc.). At least two of the first dose level of the first scan, the second dose level of the second scan, the third dose level of the third scan, the fourth dose level of the fourth scan, etc., described elsewhere in the present disclosure may be different. For instance, the first dose level may be different from the second dose level or the third dose level, or the fourth dose level. At least two of the first dose of the first scan, the second dose of the second scan, the third dose of the third scan, the fourth dose of the fourth scan, etc., described elsewhere in the present disclosure may be the same. For instance, the second dose may be the same as the third dose or the fourth dose.

In some embodiments, process 500 may be performed before the delivery of a treatment fraction. In some embodiments, process 500 is performed periodically before each treatment fraction, or every other treatment fraction, etc. In some embodiments, process 500 is performed non-periodically according to a decision made by, e.g., a doctor, the radiation therapy system 100, etc. Such a decision may be made based on an observation regarding the subject (e.g., an abrupt weight loss/gain), a testing result (e.g., the result of a blood test), information provided by the subject (e.g., a description regarding his/her own condition), or the like, or a combination thereof.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Not withstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

I claim:
1. A system, comprising:
one or more scanners;
at least one non-transitory storage medium including a set of instructions for adapting treatment plan; and
at least one processor configured to communicate with the at least one non-transitory storage medium, wherein when executing the set of instructions, the system is directed to:
obtain a planning image of a region of interest relating to a first treatment plan;
obtain a first image of the region of interest relating to a first scan of the region of interest with a first dose level delivered by the one or more scanners;
compare the planning image with the first image to generate a first comparison result;
determine whether the first comparison result satisfies a first replanning condition;
cause, in response to a determination that the first comparison result satisfies the first replanning condition, the one or more scanners to perform a second scan with a second dose level to provide a second image; and
generate a second treatment plan according to the second image,
wherein the second dose level is higher than the first dose level.

2. The system of claim 1, wherein the system is further directed to:
send an instruction to a radiation treatment device to deliver the second treatment plan to the region of interest.

3. The system of claim 1, wherein the first scan is a cone beam computed tomography (CBCT) scan, and the second scan is a multislice computed tomography (MSCT) scan.

4. The system of claim 1, wherein to compare the planning image with the first image, the system is further directed to:
determine at least one first value with respect to at least one metric based on the planning image;
determine at least one second value with respect to the at least one metric based on the first image; and
compare the at least one first value with the at least one second value.

5. The system of claim 4, wherein to determine whether the first comparison result satisfies the first replanning condition, the system is further directed to:
determine whether a difference between the first value and the second value exceeds a threshold.

6. The system of claim 4, wherein the at least one metric is associated with an anatomical feature in the region of interest.

7. The system of claim 1, wherein the system is further directed to:
send, in response to a determination that the first comparison result fails to satisfy the first replanning condition, an instruction to the radiation treatment device to deliver the first treatment plan to the region of interest.

8. The system of claim 7, wherein the system is further directed to:
obtain at least one second comparison result of at least one second treatment fraction performed prior to the first treatment fraction;
based on the first comparison result and the at least one second comparison result, determine whether a second replanning condition is satisfied;

obtain, in response to the determination that the second replanning condition is satisfied, a third image relating to a third scan of the region of interest;

determine a third treatment plan based on the third image, wherein the third scan is an MSCT scan with a third dose level delivered by MSCT;

wherein the third dose level is greater than the first dose level.

9. The system of claim 7, wherein the treatment plan includes a plurality of treatment fractions, the system is further directed to:

determine whether the first comparison result satisfies a third replanning condition;

obtain, in response to the determination that the first comparison result satisfies the third replanning condition, a fourth image relating to a fourth scan of the region of interest; and determine a fourth treatment plan based on the fourth image, wherein the fourth scan is an MSCT scan with a fourth dose level delivered by MSCT;

wherein the fourth dose level is greater than the first dose level.

10. The system of claim 1, wherein the first and second scan are multislice computed tomography (MSCT) scans.

11. The system of claim 1, wherein the first image or the second image is an MSCT image obtained by a MSCT scanner, and MSCT imaging bore of the MSCT scanner shares a common axis of rotation with a bore of a radiation treatment device.

12. A computer-implemented method for adapting a treatment plan, the method comprising the following operations performed by at least one processor:

obtaining a planning image of a region of interest relating to a first treatment fraction of a first treatment plan;

obtaining a first image of the region of interest relating to a first scan of the region of interest with a first dose level delivered by the one or more scanners;

comparing the planning image with the first image to generate a first comparison result;

determining whether the first comparison result satisfies a first replanning condition;

causing, in response to a determination that the first comparison result satisfies the first replanning condition, one or more scanners to perform a second scan with a second dose level to provide a second image; and generating a second treatment plan according to the second image, wherein the second dose level is higher than the first dose level.

13. The method of claim 12, further comprising:

sending an instruction to a radiation treatment device to deliver the second treatment plan to the region of interest.

14. The method of claim 12, wherein the first scan is a cone beam computed tomography (CBCT) scan, and the second scan is a multislice computed tomography (MSCT) scan.

15. The method of claim 12, wherein comparing the planning image with the first image, the at least one processor further comprising:

determining at least one first value with respect to at least one metric based on the planning image;

determining at least one second value with respect to the at least one metric based on the first image; and comparing the at least one first value with the at least one second value.

16. The method of claim 15, wherein determining whether the first comparison result satisfies the first replanning condition further comprising:

determining whether a difference between the first value and the second value exceeds a threshold.

17. The method of claim 15, wherein the at least one metric is associated with an anatomy feature in the region of interest.

18. The method of claim 12, further comprising:

sending, in response to the determination that the first comparison result fails to satisfy the first replanning condition, an instruction to the radiation treatment device to deliver the first treatment plan to the region of interest.

19. The method of claim 18, further comprising:

obtaining at least one second comparison result of at least one second treatment fraction performed prior to the first treatment fraction;

based on the first comparison result and the at least one second comparison result, determining whether a second replanning condition is satisfied;

obtaining, in response to the determination that the second replanning condition is satisfied, a third image relating to a third scan of the region of interest;

determining a third treatment plan based on the third image, wherein the third scan is an MSCT scan with a third dose level delivered by MSCT;

wherein the third dose level is greater than the first dose level.

20. The method of claim 18, further comprising:

determining whether the first comparison result satisfies a third replanning condition;

obtaining, in response to the determination that the first comparison result satisfies the third replanning condition, a fourth image relating to a fourth scan of the region of interest; and determining a fourth treatment plan based on the fourth image, wherein the fourth scan is an MSCT scan with a fourth dose level delivered by MSCT;

wherein the fourth dose level is greater than the first dose level.

21. The method of claim 12, wherein the first scan and the second scan are multislice computed tomography (MSCT) scans.

22. The method of claim 12, wherein the first image or the second image is an MSCT image obtained by a MSCT scanner, and MSCT imaging bore of the MSCT scanner shares a common axis of rotation with a bore of a radiation treatment device.

23. A non-transitory computer-readable storage medium including instructions that, when accessed by at least one processor of a system, causes the system to perform a method including:

obtain a planning image of a region of interest relating to a first treatment fraction of a first treatment plan;

obtain a first image of the region of interest relating to a first scan of the region of interest with a first dose level delivered by the one or more scanners;

compare the planning image with the first image to generate a first comparison result;

determine whether the first comparison result satisfies a first replanning condition;

cause, in response to a determination that the first comparison result satisfies the first replanning condition, one or more scanners to perform a second scan with a second dose level to provide a second image; and generate a second treatment plan according to the second image,
wherein the second dose level is higher than the first dose level.

* * * * *